United States Patent [19]

Talwar

[11] Patent Number: 4,780,312
[45] Date of Patent: Oct. 25, 1988

[54] BIRTH CONTROL VACCINE
[75] Inventor: Gursaran P. Talwar, New Delhi, India
[73] Assignee: National Institute of Immunology, New Delhi, India
[21] Appl. No.: 870,502
[22] Filed: Jun. 4, 1986
[30] Foreign Application Priority Data Jun. 4, 1985 [CA] Canada .................................. 483086
[51] Int. Cl.$^4$ .......................................... A61K 37/24
[52] U.S. Cl. ...................................... 424/88; 424/95; 424/105; 514/21; 530/399; 530/402; 530/403; 530/405
[58] Field of Search .......................... 424/88, 95, 105; 530/399, 402, 403, 405; 514/21

[56] References Cited

U.S. PATENT DOCUMENTS 4,161,519 7/1979 Talwar .................................. 424/88

FOREIGN PATENT DOCUMENTS 376312 9/1938 Canada .
1029656 4/1978 Canada .
1054937 5/1979 Canada .
1057742 7/1979 Canada .
1108048 9/1981 Canada .
1113389 12/1981 Canada .
1181742 1/1985 Canada .
1183527 3/1985 Canada .
1189789 7/1985 Canada .
1492445 11/1977 United Kingdom .
1505751 3/1978 United Kingdom .

OTHER PUBLICATIONS

Nash et al., J Reproductive Immunol 7, 1985, pp. 151–162.
"Immunofluorescense and Electron Microscopie Studies on Kidney, Chorid Plexus and Pituitary in Rhesus Monkeys Immunized with the Anti–hCG Vaccine Pr—B–HCG–TT", Gupta et al; Contraception (1978).
"Observations on the Antigenicity and Clinical Effects of a Candidate Antipregnancy Vaccine: B–Subunit of Human Chorionic Gonadotrophin Linked to Tetanus Toxoid", Nash et al; The American Fertility Society (1979).
"Effects of Pregnancy in Mice of Passive Immunization Against Ovine LH and Human Chorionic Gonadotrophin", Tandon et al; Journals of Reproduction & Fertility (1984).
"Important Role of the Carrier in the Induction of Antibody Response Without Freund's Complete Adjuvant Against a 'Self' Peptide Luteinizing Hormone–Releasing Hormone (LHRH)", N. Shastri et al; American Journal of Reproductive Immunology, (1981).
"Use of Anti–Gonadotrophins in Studying the Action of Gonadotrophines", N. R. Mougal; Immunization with Hormones in Reproduction Research (1975).
"Termination of Pregnancy in Macaques (Macaca radiata) Using Monkey Antiserum to Ovine Luteinizing Hormone", S. Prahalada et al (1975).
"Passive Immunization with an Antibody to the B–Subunit of Ovine Luteinizing Hormone as a Method of Early Abortion—A Feasibility Study in Monkeys (Macaca Radiata)", R. N. Mougal et al, Fertility & Sterility, (1978).
"Immunological Methods to Prevent Pregnancy", S. J. Segal; Contraception (1976).

(List continued on next page.)

Primary Examiner—Howard E. Schain
Assistant Examiner—Garnette D. Draper
Attorney, Agent, or Firm—Lorusso & Loud

[57] ABSTRACT

A polyvalent vaccine for control of fertility is disclosed, the vaccine having a multiplicity of determinant antigens in the reproductive system of mammals, the antigens being linked to at least one carrier. The precise manner of linkage can differ, and preferably more than one carrier is present thereby increasing antibody response particularly in those subjects who are poor responders when a single carrier only is used. The new vaccine thus has a multi-valent capability against the reproductive system and also preferably the capability of producing immunoprophylactic benefit against more than one health hazard.

25 Claims, 9 Drawing Sheets

OTHER PUBLICATIONS

"Anti-hCG Immunization", G. P. Talwar; *Contraception* (1978).

"Differential Affinity of Anti-Pr-B-hCG-TT Antibodies for hCG and hLH", *Contraception*, (1978).

"Discriminatory Effect of Anti-Pr-B-hCG-TT Antibodies on Neutralization of the Biological Activity of Placental and Pituitary Gonadotrpins", C. Das et al; *Contraception*, (1978).

"Progesterone Levels in Monkeys Immunized with Pr-B-hCG-TT After Injection of hLH and hCG During Luteal Phase", S. Ramakrishnan; Contraception (1978).

"Differences Between the Discriminatory Activity of Antisera Raised Against the Total Gonadotropins and the Pr-B-hCG-TT for Neutralization of hCG and LH Action", P. Mohini et al; *Contraception* (1978).

"Nature of Immune Complexes Formed in Rhesus Monkeys Immunized with Pr-B-hCG-TT on Challenge with hCG", S. Ramakrishnan; *Contraception* (1978).

"The Effectiveness in Rhesus Monkeys of an Antifertility Vaccine Based on Neutralization of Chorionic Gonadotropin", K. Sundaram et al; *Contraception* (1976).

"Human Chorionic Gonadotropin Stimulates Luteal Function in Rhesus Monkeys Immunized Against the B-Subunit of Ovine Luteinizing Hormone", R. Thau et al; *Endochronology* (1983).

"Characterization of Anti oLHB-Antibodies Acting as Contraceptives in Rhesus Monkeys. I. In Vitro Binding Properties", Y. Yamamoto et al; *Journal of Reproductive Immunology* (1982).

"Characterizations of Anti-oLHB Antibodies Acting as Contraceptives in Rhesus Monkeys, II, In Vivo Neutralizing Ability for Gonadotropic Hormones", Y. Yamamoto et al; *Journal of Reproductive Immunology* (1983).

"Effects of Immunization with the B-Subunit of Ovine Luteinizing Hormone on Corpus Luteum Function in the Rhesus Monkey", R. Thau et al; *Fertility & Sterility* (1979).

"Effects of Long-Term Immunization Against the B-Subunit of Ovine LH on Circulating Immune Complex Formation and on Arterial Changes in Rhesus Monkeys", R. Thau et al.

BIRTH CONTROL VACCINE

BACKGROUND TO THE INVENTION

1. Field of the Invention

The present invention relates to a vaccine for control of fertility and in particular to a polyvalent vaccine having a multiplicity of determinant antigens in the reproductive system linked to at least one, and preferably more than one, carrier.

2. Description of the Prior Art

The present invention is directed to an active immunological approach for control of fertility by antibodies intercepting the action of one or more gonadotropins. The pituitary luteinizing hormone (LH) and chorionic gonadotropin (CG) exercise a critical role in the regulation of fertility in primates. The former is important for ovulation and steroidogenesis, the latter for rescue of corpus luteum and maintenance of steroidogenesis up to the time of placental shift. Human chorionic gonadotropin (hCG) is an early product of trophoblast and is recognized to be essential for the establishment and sustenance of pregnancy. Both active and passive immunological approaches have been demonstrated to be effective in primates for control of fertility. Use was made in such immunizations of Freunds Complete Adjuvant (C.F.A.) which is unacceptable for eventual human use. The present invention concerns an active polyvalent vaccine which can induce the formation of antibodies in primates effective against both gonadotropins without the use of C.F.A. The vaccine of the present invention leads to the formation of antibodies capable of reacting with the complete hCG molecule consisting of both $\alpha$ and $\beta$ subunits to produce neutralization of its biological activity as well as diminish, to an extent, the bioactivity of LH. The vaccine produces antibodies devoid of cross-reactivity with body tissues and the antibody response is of controlled and reasonably long duration, providing an immunity which is reversible, free from toxicity and contra-indications to body functions and also does not cause extra hypersensitivity problems.

The anti-hCG immunization approach of the present invention is known from earlier work and in particular from the inventor's earlier Canadian Patent No. 1,054,937, issued May 22, 1979 and also Canadian Patent No. 1,057,742 (Stevens) issued July 3, 1979. However, these two investigators of anti-hCG vaccines have used fundamentally different approaches. The present inventor has used the $\beta$ subunit of the hormone hCG, while Stevens has used the 37 amino acid carboxy-terminal peptide (CTP) of the same subunit. The modes by which this "self" protein is rendered immunogenic are also different. The present inventor has utilized a carrier, such as tetanus toxoid, whereas Stevens and co-workers initially advocated haptenic modification of the protein although they subsequently opted for the carrier approach.

hCG is a glycoproteinic hormone composed of two subunits, $\alpha$ and $\beta$. The $\alpha$ subunit is common to three other pituitary hormones, TSH, LH, and FSH. It is the $\beta$ subunit which confers in each case the hormonal individuality to these hormones. Thus, the use of only the $\beta$ subunit of hCG as antigen reduces the chances that the antibodies will cross-react with the other glycoprotein hormones, in particular TSH and FSH. While the female immune system is normally tolerant to hCG and would not be expected to produce antibodies following injection of the hormone, immunogencity can be introduced by modifying the molecule either by attaching haptenic groups or by linking it to an immunogenic "carrier" protein. Thus, in aforementioned Canadian Patent No. 1,054,937 immunization is effected using a vaccine in which $\beta$hCG is chemically linked to tetanus toxoid. This vaccine produces antibodies against both the pregnancy hormone hCG as well as tetanus toxoid. However, the efficacy of the vaccine is not adequate for some "low responder" subjects whose antibody response is too low to prevent pregnancy. The marked variation (constitutional variations) in response among subjects indicates a need to modify the vaccine so that adequate antibody response is elicited in the majority, if not all, of recipients.

SUMMARY OF THE INVENTION

The present invention attempts to provide an improved immunogen for eliciting substantially higher anti-hCG antibodies in mammalian species, as compared to the $\beta$hCG-TT vaccine. The use of more than one carrier is further proposed to evoke good antibody response in low responders to a given carrier.

According to the present invention there is provided a process for the preparation of a polyvalent vaccine which comprises the steps of (a) obtaining at least two separate antigens of the reproductive system, a first being a preparation of $\beta$subunit of hCG and a second being a preparation of a sperm antigen or a heterospecies $\alpha$ or $\beta$subunit of LH, (b) obtaining a pure preparation of at least one subject-compatible carrier, (c) conjugating said at least two antigens of step (a) with said at least one carrier of step (b) by carrying out at least one step selected from the group consisting of (i) forming a composite conjugate of said at least two separate antigens linked to the same carrier, (ii) forming a physical mixture of conjugates of said at least two separate antigens each separately linked to a said carrier, (iii) associating said at least two separate antigens which are $\beta$subunit of hCG and a said hetero $\alpha$ subunit to form an annealed composite which is then conjugated with a said carrier, and, where more than one carrier is present, (iv) forming a polyvalent conjugate of at least one antigen linked both to at least one sperm antigen and to at least one carrier, and, (v) forming a conjugate of one of said antigens linked to a said carrier, and, if necessary, (d) combining two or more conjugate products from steps (i) to (v) above.

In another aspect the present invention also provides a process for the preparation of a polyvalent vaccine using more than one carrier for a mammalian subject having a low antibody response to a single carrier conjugate vaccine which comprises the steps of (a) obtaining at least two separate antigens of the reproductive system, a first being a preparation of $\beta$subunit hCG and a second being a preparation of a sperm antigen or heterospecies $\alpha$ or $\beta$subunit of LH, (b) obtaining a pure preparation of at least two subject-compatible carriers, (c) conjugating said at least two antigens of step (a) with at least one of said at least two carriers of step (b) by carrying out at least one step selected from the group consisting of (i) forming a composite conjugate of said at least two separate antigens linked to the same carrier, (ii) forming a physical mixture of conjugates of said at least two separate antigens separately linked to at least one of said carriers, (iii) associating said at least two separate antigens which are $\beta$subunit of hCG and a said hetero α subunit of LH to form an annealed composite which is then conjugated with at least one of said carriers, (iv) forming a polyvalent conjugate of at least one antigen linked both to at least one sperm antigen and to at least one carrier, and, (v) forming a conjugate of one of said antigens linked to a said carrier, and, if necessary, (d) combining two or more conjugate products from steps (i) to (v) above.

In another aspect the present invention provides a polyvalent vaccine which comprises at least two antigens of the reproductive system with the proviso that in the case of homospecies antigens the antigens are specific to the reproductive system and at least one subject compatible carrier said polyvalent vaccine being selected from the group consisting of: (i) a composite conjugate of at least two separate antigens linked to the same carrier moiety (ii) a mixture of conjugates of at least two separate antigens each separately linked to at least one carrier (iii) an annealed composite of at least two separate antigens which are $\beta$subunit of hCG and a heterospecies αsubunit; conjugated to a carrier, (iv) a polyvalent conjugate of at least one antigen linked to sperm antigen and to at least one carrier, and, (v) a mixture of at least two of (i) to (iv).

In another aspect the present invention provides a method of birth control employing the polyvalent vaccine which comprises administering said vaccine to a female mammal at a dose and frequency sufficient to prevent pregnancy.

Thus, in the present invention increased immunogenicity is achieved, and the constitutional variation or "low responder" problem is tackled by the provision of a polyvalent vaccine consisting of more than one antigen of the reproductive system linked to more than one carrier which seeks interception or neutralization in more than one manner within the reproductive system. The novel conjugates are formed with at least two antigens linked to more than one carrier(s), one of the antigens being $\beta$hCG. The new vaccine formed from these novel conjugates can be defined as having a multivalent capability against the reproductive system and a large capability of inducing good antibody response from genetically different individuals.

In one of the preferred embodiments, the $\beta$subunit of hCG is annealed to a heterospecies αsubunit, such as αoLH, and this helps to achieve the optimal configuration for hormonal activity thereby offering the possibility of producing antibodies which recognize that configuration and prevent hormone interaction with the tissue receptors. It is important to use the αsubunit of a heterospecies since the αsubunit of hCG is common to three other hormones hTSH, hFSH and hLH. Cross-reaction with hTSH and hFSH is contra-indicated and hence one cannot use the homologous α subunit (human) for achieving an optimal conformation of hCG for bioactivity. The αsubunit, for example from ovine LH, can anneal with $\beta$hCG to generate a) the optimal confirmation, b) increased immunogenicity, c) with the further advantage that no cross-reaction is produced with hTSH and hFSH.

The $\beta$subunit of hCG is included in the polyvalent vaccine of the present invention together with a sperm antigen and/or a heterospecies $\beta$subunit of LH to provide the multiplicity of antigenic determinant so that diverse antibodies are formed to intercept fertility at more than one point. These epitopes can be present in the novel polyvalent vaccine by way of a mixed conjugate in which they are both attached to the same carrier (thus forming a mixed conjugate), or can be separately attached to different molecules of the same carrier or indeed different carriers thereby creating a physical mixture of different conjugates. As a further alternative, the two antigens can be conjugated to the carrier. With the annealed composite embodiment a heterospecies αsubunit is associated with $\beta$hCG. The αsubunit may be equine, porcine, ovine, rodent or other hetero mammalian species, other than man.

With the mixed conjugate and physical mixture of different conjugate embodiments, the $\beta$subunit of a heterospecies is bonded to $\beta$hCG. Preferably the $\beta$subunit of luteinizing hormone (LH) of a heterospecies such as equine, porcine, ovine or rodent is used, and more preferably the $\beta$subunit of ovine LH. These novel conjugates appear to produce principally LH interaction and secondly counteract CG, while the annealed composite conjugate appears to principally counteract CG while interfering less with LH.

The annealed composite can replace $\beta$hCG in the mixed conjugate and physical mixture of conjugate embodiments thereby providing a vaccine with increased efficacy.

In addition, more than two antigens can be included in the vaccine in order to boost the effect of multiplicity of determinant action in the reproductive system. Thus, a sperm antigen, such as $LDHC_4$, can be included to counteract sperm and thus prevent conception. It has also been surprisingly discovered, in accordance with the present invention, that the use of a second or more carriers in the polyvalent vaccine produces increased efficacy, this being particularly useful in overcoming the low response to a given carrier as a result of constitutional variation. The use of more than one carrier also has the distinctive advantage of producing immunoprophylactic benefit against more than one health hazard.

DESCRIPTION OF THE PREFERRED EMBODIMENTS

Methods of Conjugate Preparation

Figure 1:
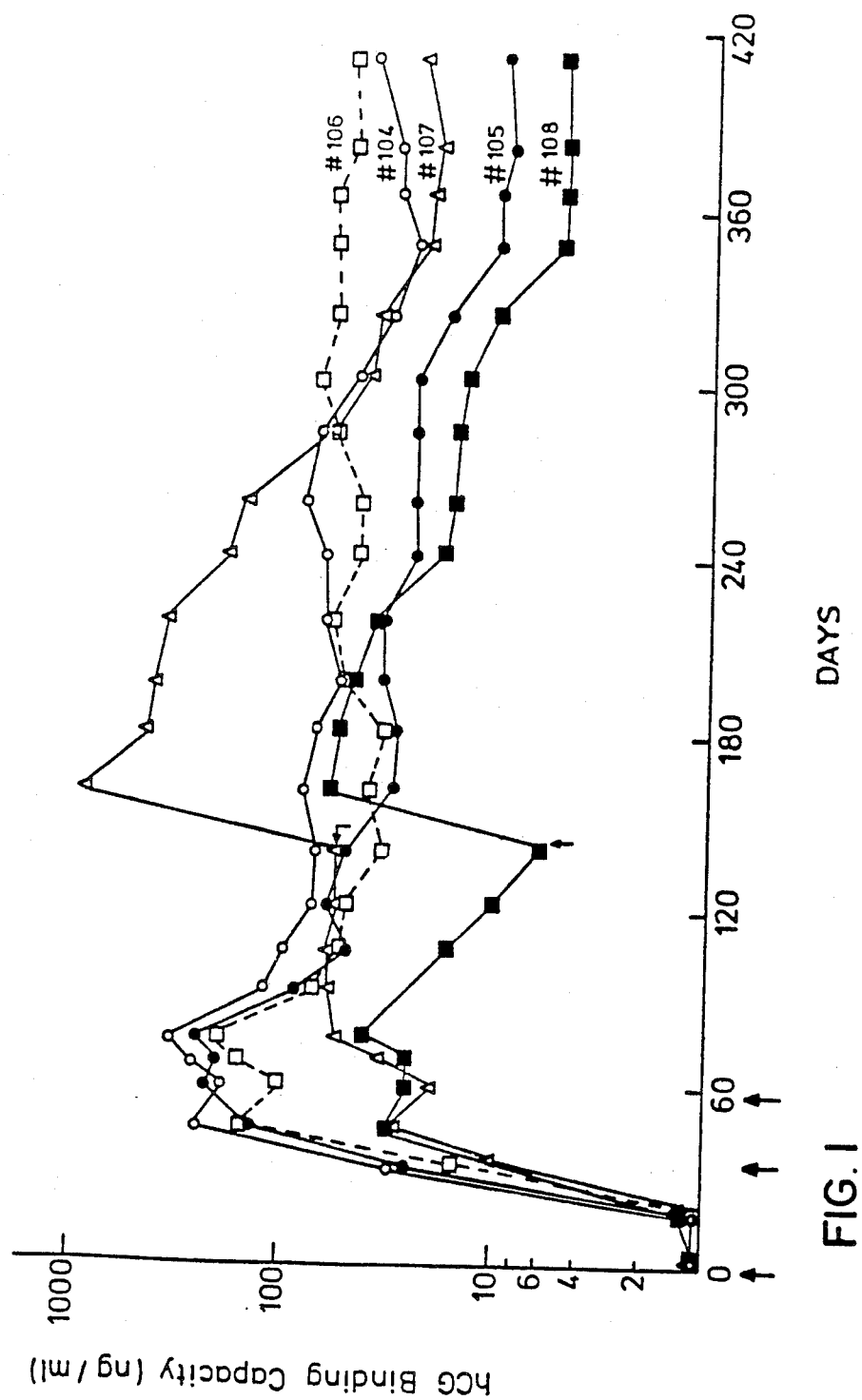
FIG. 1 indicates antibody response in five bonnet monkeys immunized with $\beta$oLH-TT, detoxified sodium phthalyl derivative of salmonella lipopolysaccharide (SPLPS) being added in the first injection only. Arrows along time scale indicate when injections were given.

Known Methods of Coupling βhCG with Tetanus Toxoid Carrier (i) In the periodate oxidation method the carbohydrate shell of the glycoprotein, in this case the subunit of the hormone, is treated with sodium meta periodate resulting in the oxidation of the alcohol groups to aldehyde which is then reacted with the $NH_2$ groups available on the carrier-tetanus toxoid in this case, in alkaline conditions to form a Schiff's base which is stabilized by the addition of the reducing agent. This design of conjugation involves only the carbohydrate part of the hormone leaving the protein untouched. The reaction does not allow for the formation of homo-conjugates of the carrier and any self coupling between the hormone subunits is minimized because of reaction conditions, namely low pH.

(ii) The use of a heterobifunctional agent such as succinimidyl 4-(N-maleimidomethyl) cyclohexane-1-carboxylate (SMCC) obviates the formation of homo-conjugates. Using this reagent, the maleimido group is introduced on to the hormone subunits using its $NH_2$ groups. The imidazole group is then attacked by a nucleophile, e.g. —SH, which is made available on the tetanus toxoid by using a reducing agent under mild conditions.

The conjugates thus formed utilize the available —$NH_2$ group of the hormone and —SH groups of the carrier. In the event SH groups are not available on the protein, they can be introduced easily.

(iii) N-Succinimidyl 3-(2-pyridyl dithio) propionate (SPDP) is another heterobifunctional agent which couples two proteins under mild conditions. The conjugating agent acts as a bridge between the two coupled proteins. The amino group of the hormone is involved in a separate reaction with the cross linking agent to ultimately yield a sulfhydryl group which is then used to form a disulfide bridge with tetanus toxoid treated separately in a similar way. This reaction design is aimed at minimizing any homo conjugate formation.

(iv) Homobifunctional reagent such as a glutaraldehyde can also be used to yield conjugates between two proteins. In the single step reaction both the proteins are mixed along with glutaraldehyde. Glutaraldehyde couples two proteins by forming a Schiff's base with $NH_2$ groups of the two protein molecules. The single step glutaraldehyde method yields conjugates which can have both homo and hetero conjugates. Glutaraldehyde forms a bridge between the two conjugated protein molecules. Glutaraldehyde can also be used as a two step procedure in which the treatment is given separately.

(v) A condensing agent like carbodiimide can be employed for forming a conjugate. 1-Ethyl-3-(3-Dimethyl amino propyl) carbodiimide (ECDI) is mixed along with the two proteins to be conjugated. The amino group of one protein reacts with the carboxyl of another to form an amide bond in the presence of carbodiimide. In the single step reaction both hetero and homo conjugates can be formed.

All the conjugation methods mentioned above can be used for preparing conjugates of the hormone subunit with the carrier. However, the preferred methods are given below with experimental details.

Conjugation of βhCG and/or βoLH with Tetanus Toxoid (TT) to form Physical Mixture of Different Conjugates Initial Mole Ratio:
βhCH:TT
10:1

(i) Periodate method of conjugation

EXAMPLE (1) 15 mg of βhCG by weight is dissolved in freshly distilled water Total volume=0.9 ml.

(2) 0.1 sodium meta periodate solution is made in freshly distilled water. 2.13 mg in 1 ml of water.

(3) To the βhCG solution 0.1 ml of 0.1M sodium meta periodate ($NaIO_4$) solution is added dropwise. The reaction is allowed to take place under constant mild agitation at room temperature (25°–30° C.) for 40 minutes.

(4) The βhCG treated with $NaIO_4$ is then dialyzed against one litre of 10 mM sodium acetate buffer, pH 4.4 at 4° C. with two changes, overnight.

(5) Tetanus toxoid 9.8 mg (Protein concentration determined by absorbance values at 235 and 280 nm) is dialyzed against 0.01M carbonate-buffer pH 9.5 so as to equilibrate the toxoid at this pH.

(6) 20–40 μl of 0.5M Carbonate buffer, pH 9.5 is added to the dialyzed βhCG solution to bring the pH to 9.5. The increment in pH is monitored carefully.

(7) Once both βhCG and TT solution are at pH 9.5 they are mixed together and left at room temperature (25°–30° C.) under constant agitation for 2–3 hours.

(8) 0.1 ml of freshly made sodium borohydride solution (4 mg/ml distilled water) is added for every ml of βhCG and TT reaction mixture. The reaction is carried out at 4° C. for 2 hours.

(9) The reduced reaction mixture is dialysed against Phosphate buffered saline (0.01M, pH 7.2, 0.9% NaCl) overnight at 4° C. with two changes.

(10) The reaction mixture is fractionated on a column packed with Sephacryl ™ S-300. The elution is carried out with 0.2M Phosphate buffer pH 7.2, 0.15M NaCl. Two ml fractions are collected and monitored for presence of protein. Peaks containing both TT and βhCG in the high molecular weight range are pooled.

The conjugates obtained by this method when run on S-300 column (85×2.5 cm) show similar protein profiles when made at different time points and have immunologically same amount of ingredients present.

(ii) SMCC Method of Conjugation

EXAMPLE (1) 15 mg of βhCG is dissolved in 0.9 ml of 0.1M phosphate buffered saline pH 6.9.

(2) 6.6 mg of succinimidyl 4 (N-Maleimidomethyl) cyclohexane-1-carboxylate (SMCC) is dissolved in 1 ml of dimethyl formamide to yield a solution of 20 mM concentration. 100 μl of this SMCC solution is added dropwise while shaking into βhCG solution. The reaction is allowed to continue for 60 minutes at room temperature (25°–30° C.).

(3) The βhCG solution with SMCC is loaded on a Sephadex ™ G-25 column (20×1.5 cm) equilibrated with 0.1M phosphate buffered saline pH 6.9 and 5 mM ethylenediaminetetraacetic acid (EDTA) and thoroughly gassed with nitrogen. The first peak containing activated βhCG is pooled and frozen immediately.

(4) To 9.8 mg (protein content) purified tetanus toxoid contained in 0.9 PBS 0.1M, pH 6.0 100 μl 50 mM mercaptoethanol is added and the reaction carried out for 45 minutes at 37° C.

(5) The mercaptoethanol treated TT is loaded on a Sephadex ™ G-25 column (20×1.5 cms) equilibrated with acetate buffered saline 0.01M, pH 4.7, containing 5 mM EDTA and well gassed with nitrogen. The first peak collected in tubes pre-treated with nitrogen gas is pooled.

(6) TT treated with mercaptoethanol and βhCG solution with SMCC are then mixed and left in the refrigerator (at 4° C.) for 36 to 48 hours.

(7) The conjugate is finally fractionated on Sephacryl ™ S-300 column using (85×2.5 cm) phosphate buffer 0.2M pH 7.2 and 0.15M sodium chloride. 2 ml fractions are collected and the protein peaks are checked for the presence of βhCG and TT. High molecular weight peak having both βhCG and TT is pooled.

Conjugation of βhCG and βoLH on the same Carrier Molecule, Tetanus Toxoid (TT) by SPDP Method to form Mixed Conjugate Initial Mole Ratio:
βoLH+βhCG:TT
17:1
16 mg: 6 mg 1. 16 mg of βoLH and βhCG, mixed in equal proportions are dissolved in sodium phosphate buffer (0.1M, pH 7.5) with sodium chloride (0.1M)

2. (i) SPDP dissolved in ethanol is added to the gonadotropin solution to yield a final concentration of 2.5 moles for every mole of gonadotropin. The mixture is allowed to react for 25 minutes at room temperature.

(ii) 200 moles of SPDP dissolved in ethanol are mixed for every mole of tetanus toxoid (6 mg in Phosphate buffer 0.1M, pH 7.5 with NaCl 0.1M) and the mixture allowed to react for 2 hours under constant mild agitation at room temperature.

3. Both activated Gonadotropin and TT containing excess SPDP are run on separate columns of Sephadex ™ G-25 (20×1.5 cm) to remove the reagent. The gonadotropin is run on a column equilibrated with sodium phosphate buffer (0.1M, pH 7.5 with sodium chloride 0.1M). Whereas tetanus toxoid is run on a column equilibrated with sodium acetate buffer 0.1M, pH 4.5, containing 0.1M sodium chloride.

4. TT is reduced by adding dithio-threitol to attain a final concentration of 50 mM. The reaction is carried out in acetate buffer pH 4.5, 0.1M, with sodium chloride 0.1M, at room temperature for 30 minutes.

5. After 30 minutes the reduced TT is separated from the excess reducing agent and pryridine 2-thione by passing it through a Sephadex ™ G-25 column equilibrated with phosphate buffer (0.1M, pH 7.5) with sodium chloride, 0.1M.

6. The gonadotropins to which 2 pyridyl disulphide have been introduced are mixed with the reduced TT and the mixture left at 4° C. for 48 hours.

To monitor the reaction spectrophotometrically aliquots are taken out immediately after mixing the two reactants, and after completion of the reaction, and the absorbance read at 343 nm. (molar extinction coefficient of pyridine 2-thione at 343 nm=$8.08\times10^3 M^{-1}cm^{-1}$).

The concentration of pyridine 2-thione released is equivalent to the number of gonadotropin subunit coupling to tetanus toxoid.

7. The conjugate is finally chromatographed on Sephacryl S-300 as detailed in other methods.

Preparation of Annealed Composite of αoLH.βhCG

αoLH and βhCG are mixed in a ratio of 2:1 in sodium acetate buffer 0.5M, pH 6.0 containing 10 mM sodium azide. The solution containing the subunits is kept under constant mild agitation at room temperature (25° C.) for 15–18 hours.

To monitor the efficiency of annealing an aliquot (10 μl) of the mixture is taken at the start and mixed with 1 ml of 40 μM 8-anilino-1-naphthalenesulfonic acid, Magnesium salt(ANS) and fluorescence measured at the following wavelengths (Exc) excitation wavelength 360 nm
(Emm) emission wavelength 480 nm No fluorescence with dissociated subunit is obtained but is given by the associated hormone.

The fluorescence is observed exactly in a similar way taking aliquots at 4 hour intervals until it fails to register any increase. Once the fluorescence has stabilized, maximum annealing has been achieved. The annealed material is then passed over a Sephadex ™ G-75 column and the high molecular weight protein peak collected and checked for gonadotropin activity. The elution buffer used is phosphate buffer 0.2M, pH 7.2, containing 0.15M sodium chloride.

Conjugation of the annealed composite to a desired carrier can be carried out by known methods. In particular the annealed product is conjugated to tetanus toxoid using SPDP in the same manner as βhCG.

Conjugation of βhCG with Cholera Toxin B-Chain 1. 10.5 mg βhCG in 1.0 ml of distilled water was treated with 0.6 ml of 0.1M sodium meta periodate in distilled water at 4° C. for 17 hours with occasional mixing.

2. The mixture was dialyzed against 1.0mM sodium acetate, pH 4.4 at 4° C. Three changes at six hourly interval with 500 ml sodium acetate buffer were made.

3. The pH of the mixture was raised to 9.0–9.5 by adding 0.02 ml of 0.2M sodium carbonate/bicarbonate, pH 9.5.

4. 3.422 mg of cholera toxin B-chain in 1 ml of 0.01M sodium carbonate/bicarbonate buffer, pH 9.5 was immediately added to the above mixture in the ice bath, stirred and kept at 4° C. for 17 hours.

5. To the reaction mixture was then added 0.1 ml of freshly prepared sodium borohydride (4 mg/ml in distilled water) and kept for two hours at 4° C.

6. The conjugate material in lots of 2.5 ml was separated from unconjugated material by chromatography on Sepharose ™ 6-B column (42×1.5 cm).

The conjugated material eluted in the void volume of the column. The descending half of the peak showed unresolved components. Some fractions were pooled and rechromatographed on the same column. Rechromatograph of the pooled fraction gave a homogeneous symmetrical peak.

In a typical preparation, the material eluted in void volume accounted for about 51% of the total material eluted in all the three peaks. Upon rechromatography, the purified CHB-βhCG conjugate recovered was of the order of 36% of the total material.

Female bonnet monkeys (Macaca radiata) of proven fertility (carrying either pups or lactating at time of supply) were immunized with the conjugates, βhCG-TT, βoLH-TT, βoLH-TT-βhCG, βhCG-TT+βoLH-TT, (αoLH.βhCG)-TT all absorbed on alum. Three injections containing 50 μg gonadotropin equivalent at monthly interval were given intramuscularly at two contralateral sites. In the first injection only 1 mg SPLPS was added. Animals with low titers were given a booster injection with the respective antigen on day 145 along with a non-toxic metabolizable lipidic emulsion, Leiras basic adjuvant (Leira Huhtamaki, Turku, Finland).

Adult female rats weighing 200–300 g were also immunized with (αoLH.βhCG)-TT and βhCG-TT conjugates (10 μg gonadotropin). The first injection was given with SPLPS after absorbing on alum, the following one with alum only.

Sera were collected at intervals and stored at −20° C. until used. The hCG binding capacity of the antisera was determined by methods described in Shastri et al, Contraception 18, 23 (1978).

Antibody response was generated in monkeys with βoLH without the use of Freund's complete adjuvant (FCA) when it was injected as a conjugate with the carrier tetanus toxoid (TT). FIG. 1 gives the kinetics of response in five bonnet monkeys immunized with 50 μg of βoLH-TT adsorbed on alum, 1 mg detoxified non-pyrogenic SPLPS was added in the first injection. Three of the five monkeys had peak titers between 200–320 ng/ml expressed as hCG binding capacity. The extensive known studies have indicated the virtual identity of the hLH and hCG reactivity of monkey sera immunized with βoLH. Two monkeys were relatively low responders, in which the primary immunization gave rise to optimum titers of 40–60 ng/ml. These were given a fourth booster injection on day 145 which increased the titers to 60 ng/ml and 900 ng/ml respectively.

Figure 2:
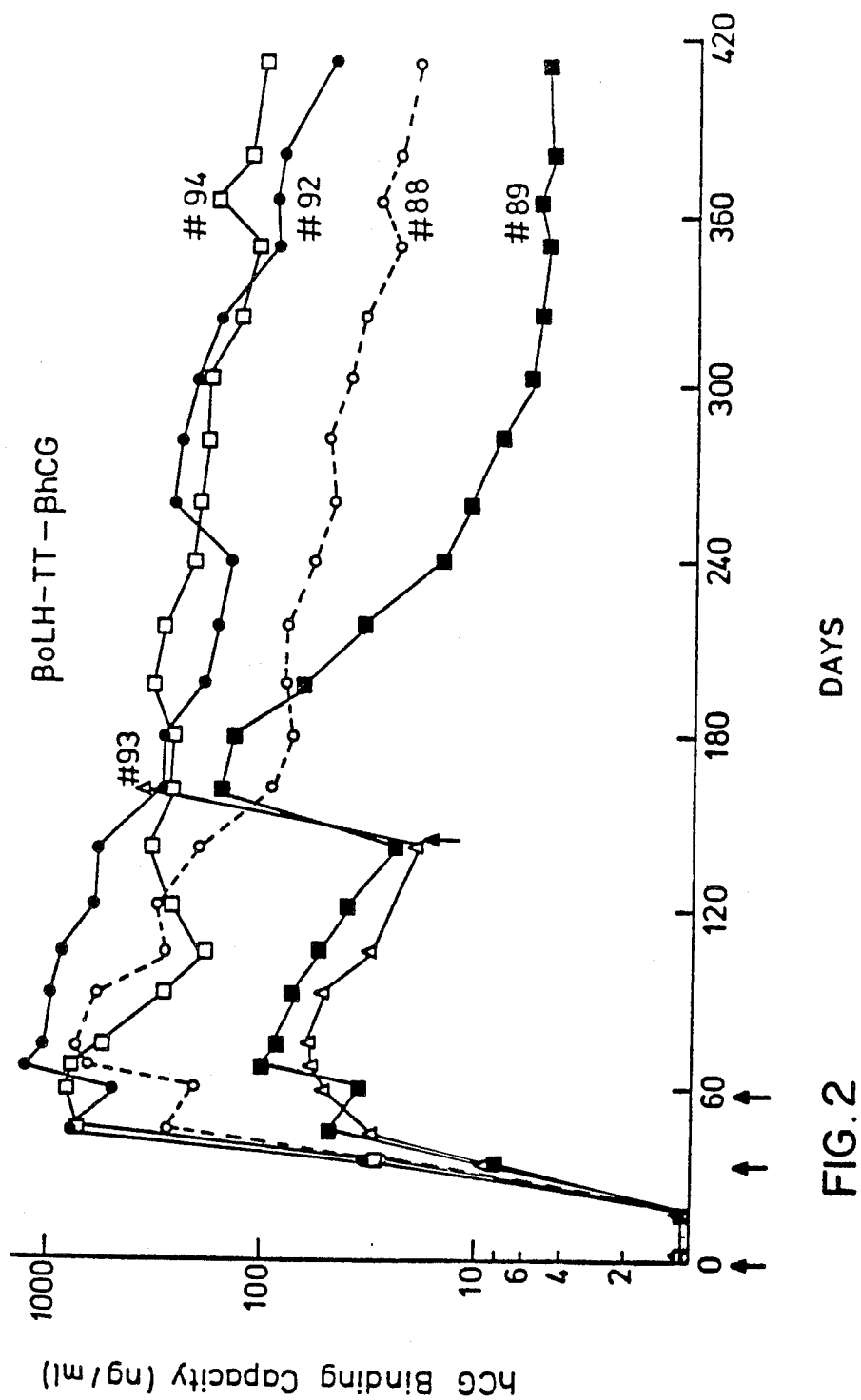
FIG. 2 indicates antibody response in five bonnet monkeys immunized with $\beta$oLH-TT-$\beta$hCG mixed conjugate.

However a considerably improved antibody response was attained when immunization was carried out with βoLH and βhCG tagged to a common carrier, TT, to form a mixed conjugate βoLH-TT-βhCG. Injections with the same dose of the antigen (50 g equivalent of gonadotropin) gave in three monkeys peak titers between 750 to 1300 ng/ml (FIG. 2). The response was sustained and above 100 ng/ml in two monkeys for nearly a year. Assuming 60 ng/ml of anti-hCG titers as a cut off point for efficacy, the area under the curves above this threshold for the two formulations is given in Table 1. The cumulative antibody response with the mixed conjugate was about 13 times higher than with βoLH on the same carrier employing a common dose and immunization schedule. The time duration over which this response was manifest was twice as long with βoLH-TT-βhCG than with βoLH-TT. The βhCG-TT immunized monkeys (FIG. 3) following the same dose and time schedule produced after the 3 primary injections, peak titers ranging from 7–500 ng/ml, the fourth booster injection raising the titers to 70–800 ng/ml. Monkey No. 93 died on day 171 after immunization due to diarrhea. Autopsy did not reveal any pathology associated with immunization.

Figure 4:
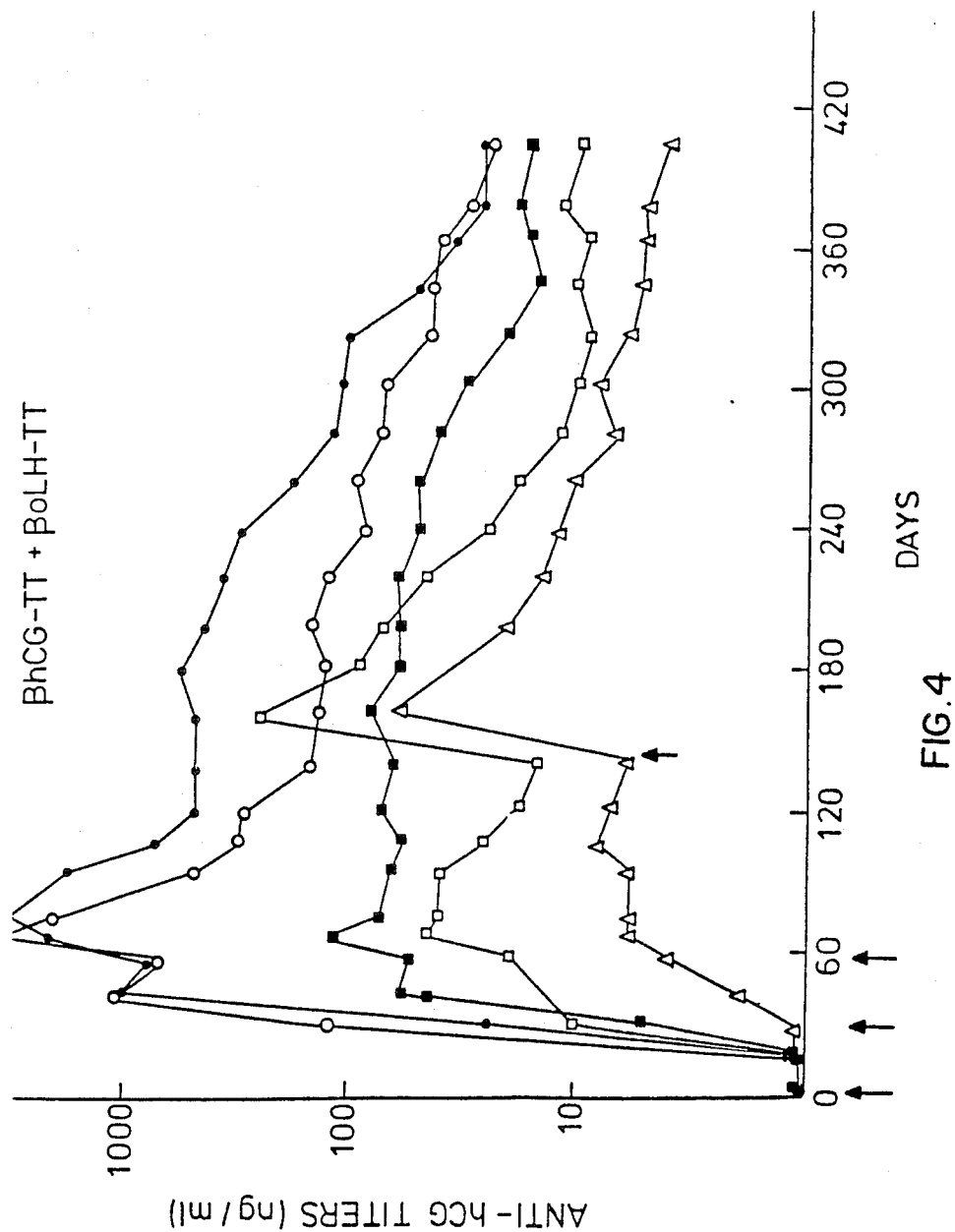
FIG. 4 indicates antibody response in five bonnet monkeys immunized with $\beta$oLH-TT+$\beta$hCG-TT physical mixture, i.e. an equal mixture of $\beta$oLH-TT and $\beta$hCG-TT (on the basis of gonadotropin subunits).

The mixed formulation could consist of the two types of subunits tagged to a common carrier (βoLH-TT-βhCG) or as an alternate each one of them could be coupled individually to the carrier and employed as a physical mixture (βoLH-TT and βhCG-TT). FIG. 4 summarizes the results of the experiment in which the monkeys received 25 μg each of βoLH-TT and βhCG-TT. Two of the monkeys 110 and 111 had peak titers of 3200 and 3500 ng/ml respectively. The characteristics of the antibodies were similar to those generated by βoLH-TT-βhCG.

Figure 3:
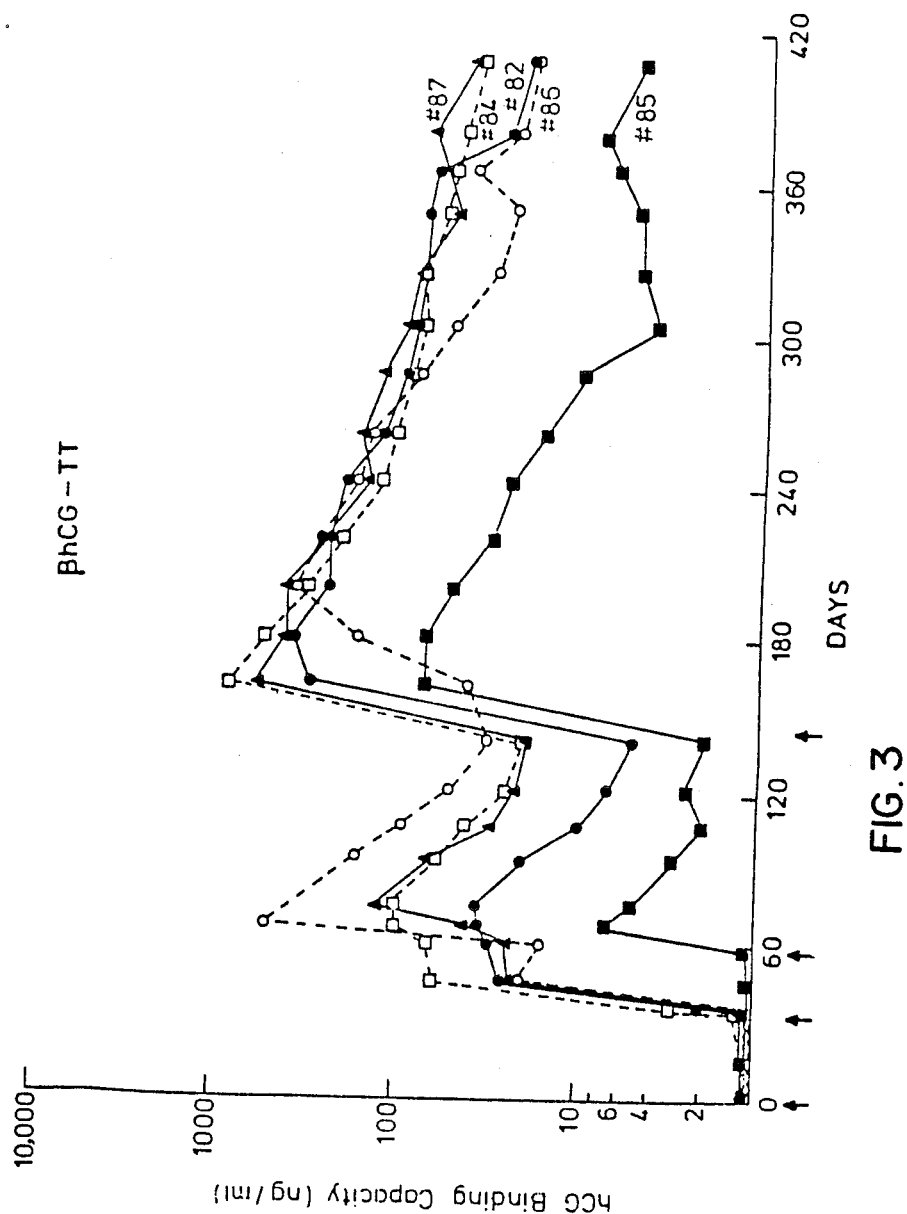
FIG. 3 indicates antibody response in five bonnet monkeys immunized with $\beta$hCG-TT. All monkeys received a fourth booster injection.
Figure 6:
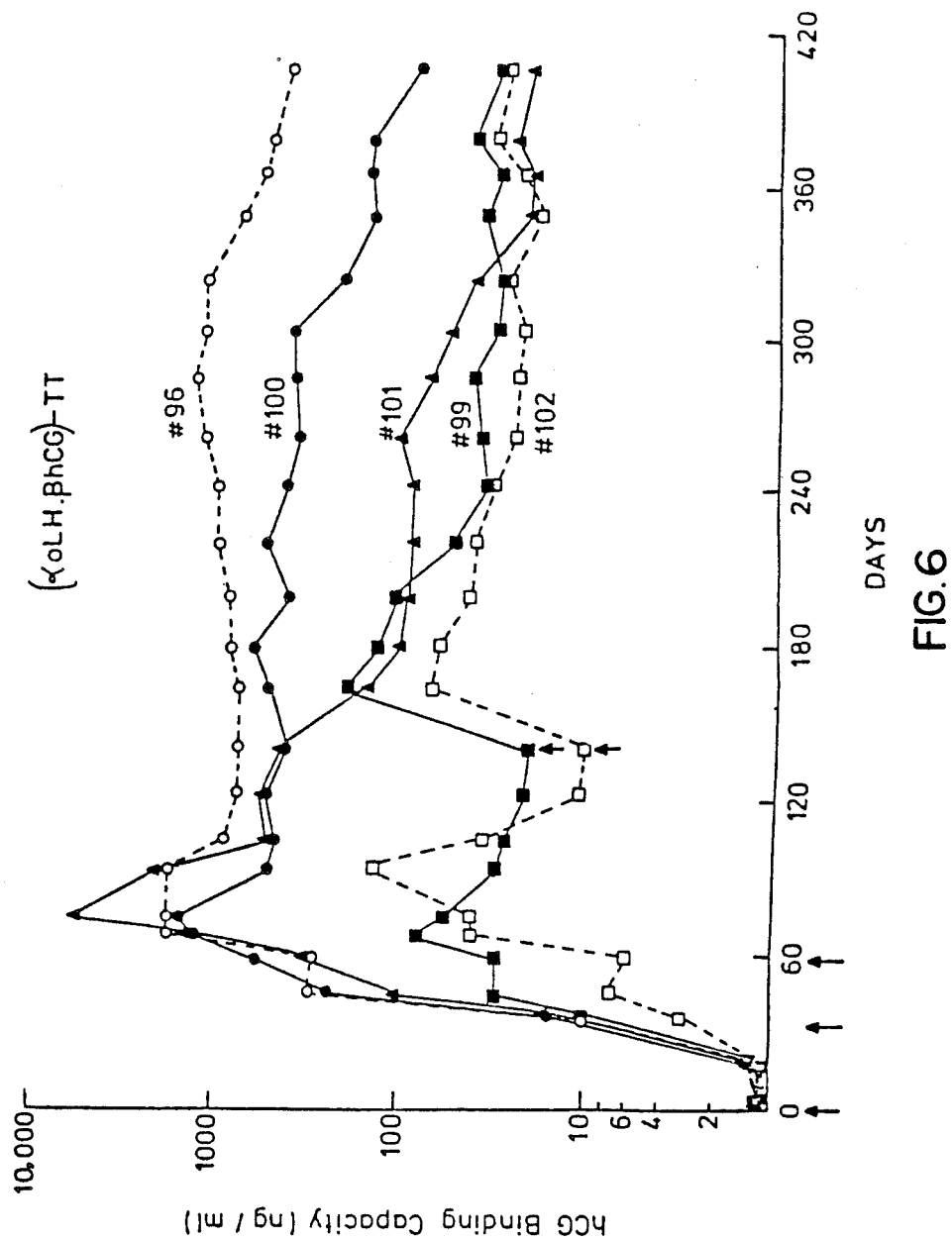
FIG. 6 indicates antibody response in five bonnet monkeys immunized with (αoLH.$\beta$hCG)-TT annealed composite conjugate.

FIG. 6 gives the antibody titers in a group of five monkeys immunized with (αoLH.βhCG)-TT conjugate. Three of the five monkeys produced high titers of antibodies (1500 ng/ml to 5200 ng/ml). The antibodies started appearing after the first injection around day 33, reached maxima at 75 days and then declined to a level which was more or less sustained for 5 to 10 months. Using a similar injection schedule and equivalent dose, the antibody response with the known vaccine βhCG-TT was distinctly lower (FIG. 3). The latent period of antibody titers was 45 days. The titers reached after three primary injections were between 7–500 ng/ml with a tendency to decline fairly rapidly necessitating an additional booster injection on day 145. The antibody titers after the fourth injection ranged from 70 ng/ml to 800 ng/ml. The use of βhCG annealed to αoLH in the conjugate was thus distinctly beneficial in raising the level of immune response, employing non-toxic adjuvants. Assuming that the normal threshold for protection against pregnancy be 60 ng/ml of hCG binding capacity, the antibody response above this level in good responders and the duration over which it lasts for the two formulation is given in Table 1a. It may be pointed out that fixing the threshold of 60 ng/ml is a tentative criteria as most monkeys in the colony under test with various formulations became pregnant at titers below 50 ng/ml. There were however a few which required titers above 140 ng/ml to remain infertile. The degree of cross-reaction of the anti-hCG antibodies with monkey chorionic gonadotropin (mCG) is low and varies from animal to animal depending on the determinants to which the antibodies are raised.

Figure 7:
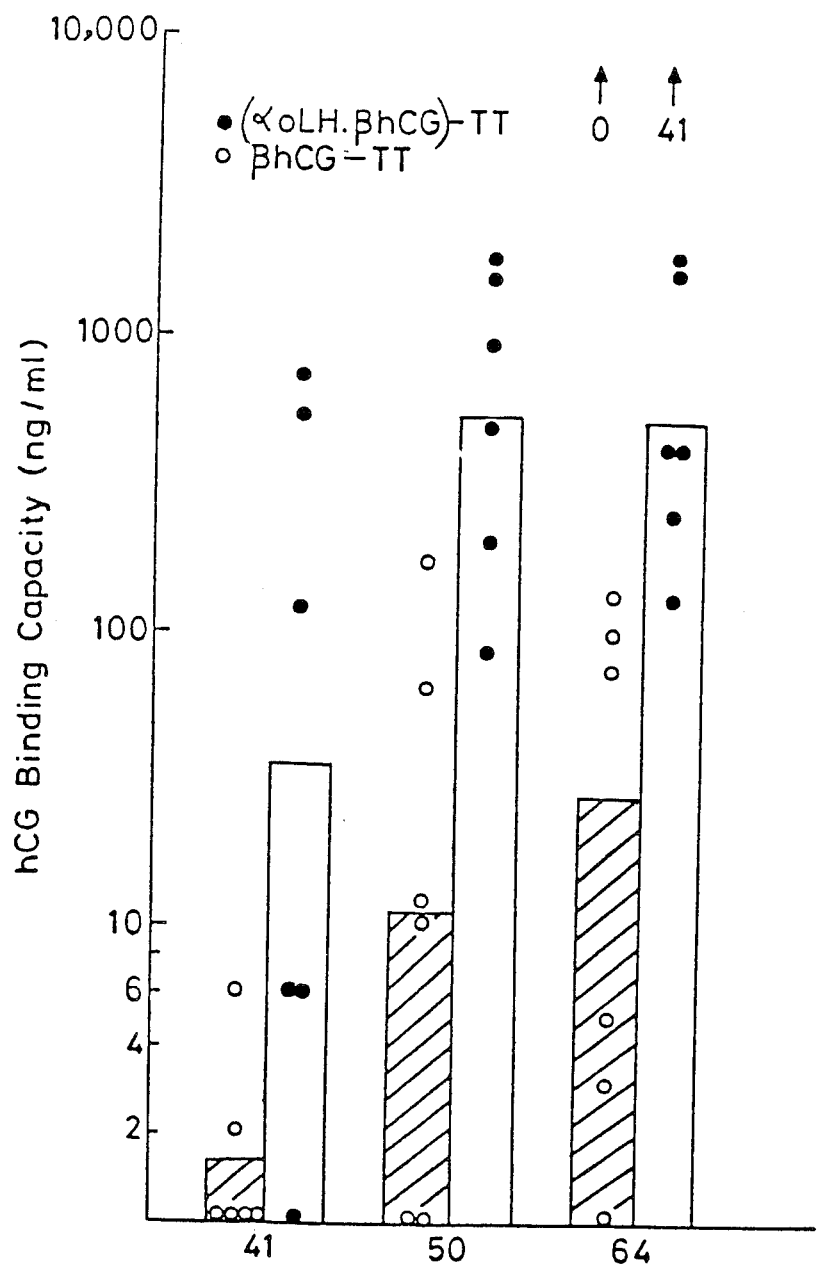
FIG. 7 indicates antibody response in rats after immunization with either (αoLH.$\beta$hCG)-TT or $\beta$hCG-TT. The animals were given two injections (10 $\mu$g gonadotropin) on day 0 and 41. The titers were determined on day 41, 50 and 64 after start of immunization. Points give the individual titers and bars represent the geometric mean.

(αoLH.βhCG)-TT was also found superior to βhCG-TT for induction of anti-hCG response in rats (FIG. 7). A regimen of two injections was given at 6 weekly intervals. Following the first injection, 5 out of 6 rats immunized with (αoLH.βhCG)-TT had circulating antibodies (6 to 720 ng/ml) whereas in those immunized with βhCG-TT only two had antibodies (2 to 6 ng/ml). After the second injection, 5 out of 6 rats immunized with βhCG-TT had antibody titers ranging from 3 ng/ml to 130 ng/ml on day 64. On the other hand in case of (αoLH.βhCG)-TT, 6 out of 6 rats had antibodies in circulation at this time and their titers were from 130 ng/ml to 1870 ng/ml.

Characteristics of Antibodies

The association constant (Ka) of antibodies for binding with hCG is given in Table 2 for the mixed conjugate formulation and for βoLH-TT. Both antigens induced antibodies of high affinities. The cross-reactivity of antibodies generated by the two immunogens with various pituitary hormones is given in Table 3. No cross-reaction with hFSH and hTSH was observed in either case. Both formulations produced antibodies reacting with hCG and hLH. Some sera generated by βoLH-TT cross-reacted with hCG and hLH to nearly the same extent, those with βoLH-TT-βhCG had slightly greater cross-reactivity with hCG.

Association constant (Ka) of the antibodies induced by the new composition, (αoLH.βhCG)-TT was from $1 \times 10^9$ to $2 \times 10^{10} M^{-1}$ for binding with hCG (Table 2a). The presence of αoLH as an associated subnit did not lead to cross-reactive antibodies to human thyroid stimulating hormone (hTSH) and follicle stimulating hormone (hFSH) (Table 3a). The cross-reactivity with human leutinizing hormone (hLH) was of the order of 44 to 80% (Table 3a). Recent studies have demonstrated the lack of hazard of antibodies cross-reactive with LH after five years of hyper immunization. The cross-reactivity with LH was in fact beneficial and contributory to control of fertility. (Thau, R. B., Sundaram, K., Thornton, Y. S. and Seidman, L. S. (1979) "Fertil. and Steril.", 31, 200–204)

Reproductive Status

Immunized monkeys were mated continuously with males. The antifertility effect of these formulations and titers preventing pregnancy are given in Table 4. However, some animals shown in Table 5 became pregnant when the antibody titers were low.

Monkeys 92 and 94 immunized with the βoLH-TT-βhCG were mated 7 and 5 times respectively with males of proven fertility. Out of these 6 and 3 cycles were confirmed to be ovulatory by progesterone estimations. In the colony, continuous caging of bonnet female monkeys with males results in 70% of animals becoming pregnant in the first month and the remaining 30% in the following month. These immunized monkeys were thus apparently protected from becoming pregnant. The antibody titers during this period ranged from 80–800 ng/ml in these monkeys. Monkeys No. 88 and 89 became pregnant when the antibody titers were 35 and 4 ng/ml respectively. These observations are consistent with those of others and our own where fertility is observed to be regained in primates at low antibody titers.

In βoLH-TT immunized animals, monkey No. 106 was mated six times and all the six cycles were ovulatory. She did not conceive. The prevailing antibody titers in this monkey were between 60–200 ng/ml. Monkey No. 104 remained protected in three matings carried out during the period when antibody titers were 120–150 ng/ml. Monkey No. 105, 107 and 108 became pregnant at time points at which antibody titers were 120, 30 and 10 ng/ml respectively. It may be mentioned that the titers described are against hCG, their cross-reactivity with the bonnet CG is not known. The cross-reactivity of anti hCG antibodies with primate CG is usually of a lower order; in baboons it has been describe to be between 2 to 10%. The wide variation in primates of the amount of CG produced during pregnancy from animal to animal has also been reported (10–50 IU/ml).

Immunization with the more immunogenic conjugate (αoLH.βhCG)-TT of the present invention did not lead to disturbances in reproductive functions in four monkeys out of five which kept ovulating normally. Monkey No. 102 developed anovulatory cycles. It had however low antibody titers indicating that it was not related to immunization. Some control untreated monkeys maintained in captivity also become anovulatory. Two of the monkeys (Nos. 96 and 101), who to begin with were of proven fertility did not become pregnant in spite of repeated matings (6 and 3) respectively) with males having sired off-spring in the colony. The antibody titers during this period ranged in these monkeys from 400–2600 ng/ml. The fertility rate amongst untreated animals in the colony is between 50–75% depending on whether they are mated intermittently (day 9–14 of the cycle) or mated continuously. Monkey No. 99 became pregnant at 30 ng/ml antibody titer. Monkey No. 100 did not become pregnant on mating twice with males of proven fertility, the antibody titer during the period was between 200–360 ng/ml. It became pregnant when the antibody titer was 140 ng/ml. The titer described is against hCG and not mCG, which could not be determined due to non-availability of bonnet monkey CG.

Organ, Metabolic Functions and Tissue Auto Antibodies

All conjugates are well tolerated. No local reaction was noted at the site of injection. Acute and subacute toxicology studies revealed no side effects. No significant abnormality in metabolic and organ functions was observed in the hematological and clinical chemistry parameters determined at an interval of three months over a period of fifteen months. The antibodies were devoid of smooth muscle, parietal cell, thyroid, microsomal, thyroglobulin, antinuclear, anti-mitochondrial, anti-DNA, C-reactive protein, rheumatoid factor and anti-islets cell reactivity.

The case of low responders

Figure 5:
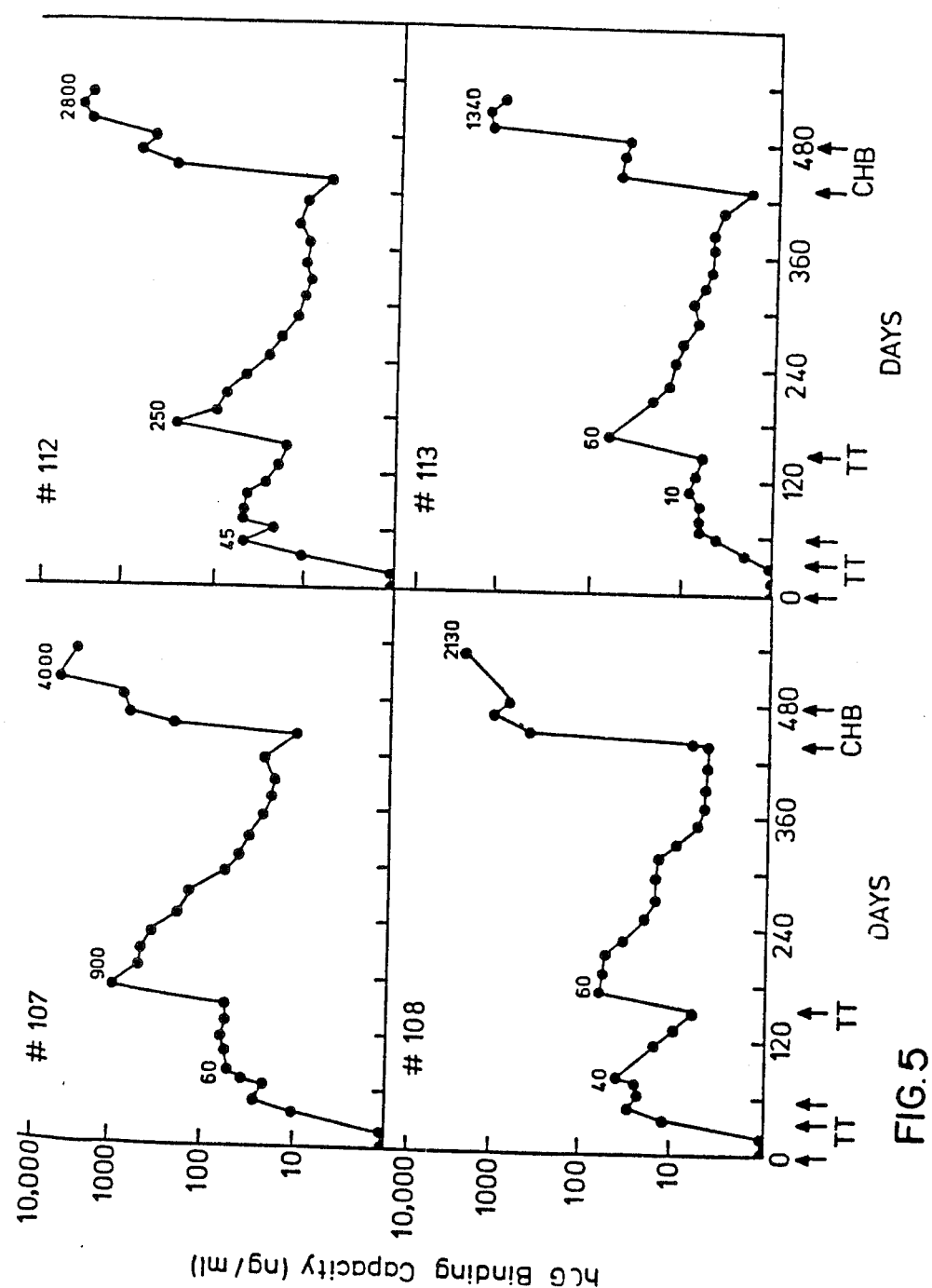
FIG. 5 indicates the effect of immunization with an altered carrier on antibody response in bonnet monkeys which were low responders to $\beta$hCG-TT+$\beta$oLH-TT (monkeys No. 112, 113) or to $\beta$oLH-TT (monkeys No. 107-108). 50 $\mu$g of $\beta$hCG linked to cholera toxin B chain was injected on days 431 and 479.

In each formulation, 2 to 3 monkeys were relative low-responders. Additional booster injections with the same conjugate improved responsiveness to some extent. (FIG. 1, 2 and 5). An alternate carrier, cholera toxin B-chain was utilized to see whether the responsiveness of such monkeys could be improved. FIG. 5 gives the results of two monkeys immunized with the physical mixture of βoLH-TT and βhCG-TT. The peak titers after primary immunization in the monkey 113 and 112 were 10 ng/ml and 45 ng/ml respectively. A booster on day 145 with the same conjugate increased the titers to 60 ng/ml and 250 ng/ml. They were then immunized on day 431 and 479 with βhCG conjugated to cholera toxin-B chain which boosted the titers to 1340 ng/ml and 2800 ng/ml, hCG binding capacity. Similar observations were made for two low responders to βoLH-TT. The peak titers after 3 injections in the monkey 107 and 108 were 60 and 40 ng/m¹. A booster on day 145 with the same conjugate increased the titer to 900 ng/ml and 60 ng/ml respectively. They were immunized on day 431 and 479 with βhCG conjugated to cholera toxin B-chain which boosted the titers to 4000 and 2130 ng/ml hCG binding capacity.

Figure 8:
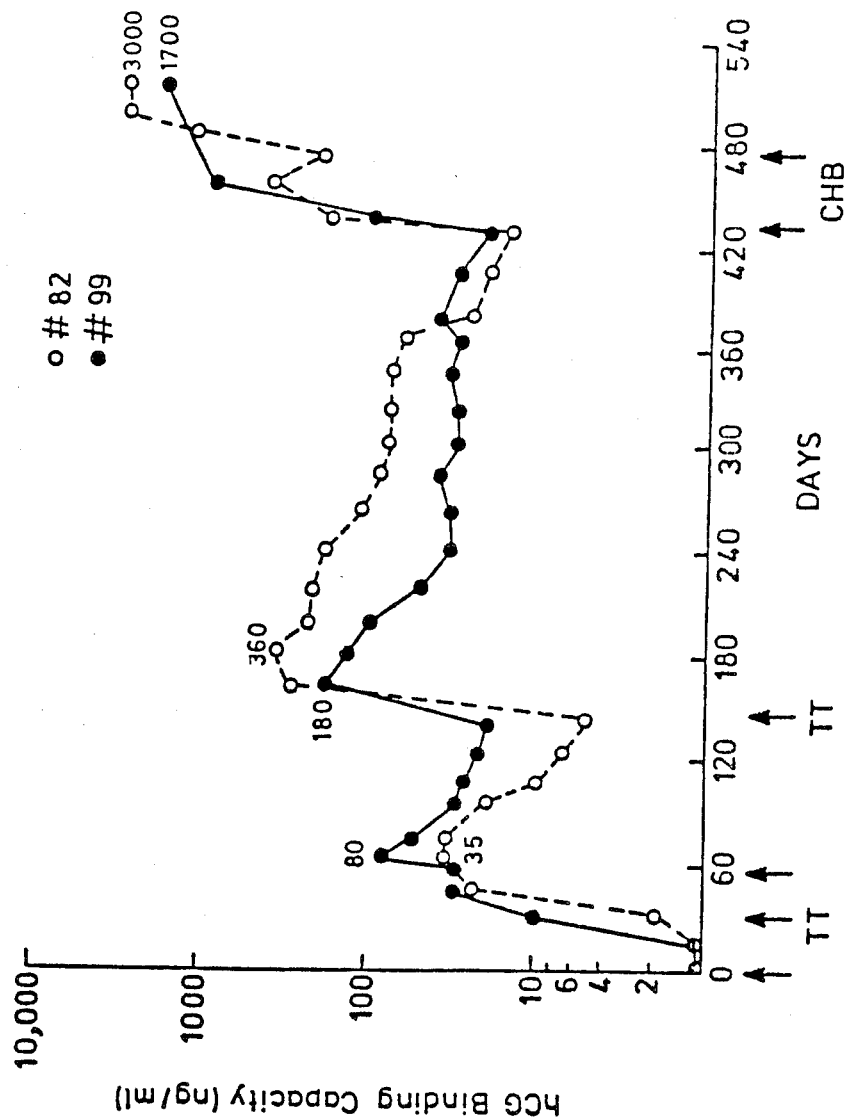
FIG. 8 indicates the effect of immunization of monkeys with cholera toxin B-chain (CHB) as carrier in monkeys producing antibodies of low titers with TT as a carrier. Monkey 82 was immunized with βhCG-TT and later with βhCG-CHB, monkey 99 with (αoLH.βhCG)-TT initially and later with αoLH.βhCG linked to CHB.
Figure 9:
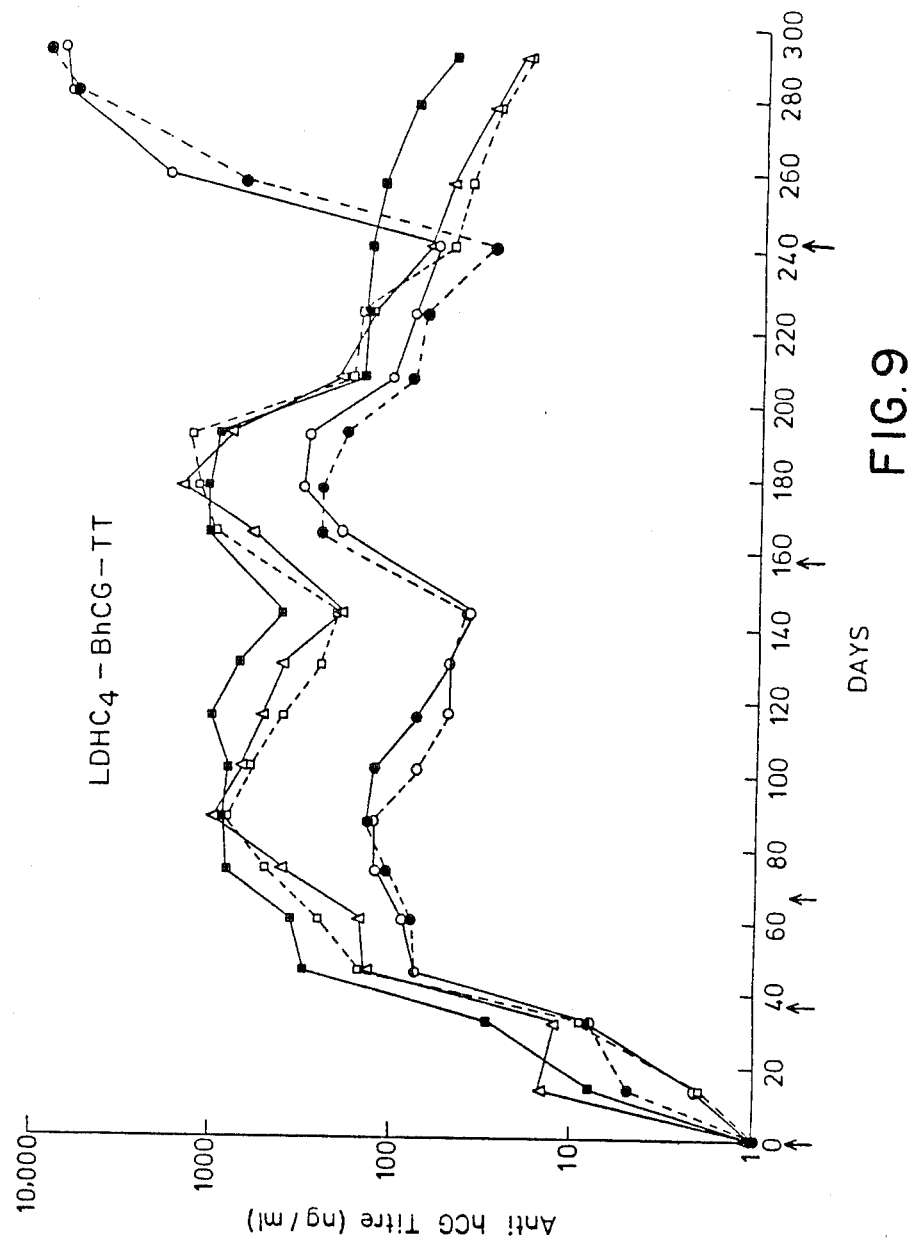
FIG. 9 indicates anti-hCG response in 5 bonnet monkeys immunized with LDHC$_4$-βhCG-TT conjugate. Arrows indicate three primary injections given at monthly intervals followed by a booster injection on day 158.

Monkey No. 99 was a low responder to (αoLH.βhCG)-TT. Being given that the carrier would be mobilizing helper 'T' cell function, it could be hypothesised that the low titer in this animal could be due to its low responsiveness to TT. However when the immunogen was conjugated to an alternate carrier, the B chain of cholera toxin (CHB), a boost in the anti-hCG response was noted. The animal had a peak titer of 80 ng/ml after the first three primary injections, an additional booster with the same carrier raised the antibody titer to 180 ng/ml (FIG. 8). On immunization with CHB as carrier, the titers reached 1700 ng/ml. Similar observations were made for low responders amongst monkeys immunized with βhCG-TT (FIG. 8).

The feasibility of controlling fertility with antibodies generated by βoLH has already been demonstrated in a variety of animal species including the subhuman primates. The procedure adopted however demanded the use of Freund's complete adjuvant (CFA). CFA is not permissible for human use. An eventual birth control vaccine based on this antigen would require an approach which can lead to the formation of enough antibodies without the use of CFA. Linkage of βoLH to tetanus toxoid (TT) has rendered it immunogenic in monkeys with a simple permissible adjuvant, aluminum hydroxide. Detoxified sodium phthalyl derivative of salmonella lipopolysaccharide (SPLPS) was employed in the first injection only. SPLPS has been used in clinical trials without adverse effects (Elin, R. J., Wolff, S. M., McAdam, K. P. W. J., Chedid, L., Audibert, F., Bernard, C. and Oberling, F.: Properties of reference *E. coli* endotoxin and its phthalylated derivative in humans. *J. Infect. Diseases* 144, 329, 1981.) The antibody response was of a fairly long duration (over a year) in good responders. High titer monkeys were protected against pregnancy during repeated matings with males of proven fertility. Fertility was regained at low titers. The antibodies reacted with both hCG and hLH but not with hTSH and hFSH.

hCG, a glycoproteinic hormone is composed of two subunits The association of the two subunits generates a conformation fitting optimally the receptors on the male and female steroid hormone-producing cells. Dissociation leads to a conformation with 400 fold reduced potency of stimulating steroido-genesis even though the βsubunit of hCG retains a residual form binding less well to the receptor and stimulating the hormonal response. (Ramakrishnan, S., Das, C. and Talwar, G. P. (1978) Biochemical Journal, 176, 599–602) It is thus clear that the biologically effective optimal conformation of the hormone results only on its association with the αsubunit. This conformation is important for inducing antibodies with optimal potential of neutralizing the bioactivity of this hormone.

The idea of annealing βhCG to βoLH was to generate the conformation optimally fitting into tissue receptors, which hopefully could induce conformational antibodies interfering with the hormone-target tissue interaction. Homologous αsubunit was not advisable as it would have led to the induction of antibodies cross-reactive with hFSH and hTSH, both of which contain a common αsubunit. The αsubunit of oLH on the other hand did not give cross-reactive antibodies to the human hormones. Surprisingly, annealing βhCG to αoLH gives rise to a receptor binding potency two times higher and steroidogenic potency three times higher than the homologous combine of the human hormonal subunits.

(αoLH.βhCG)-TT is a distinctively better immunogen than βhCG-TT in both rodents and bonnet monkeys. The increment in anti-hCG peak titers (geometric means) by the use of the new conjugate composition was of the order of 18 and 10 fold in rodents and monkeys respectively. This appears to be adequate for protection against pregnancy as judged by the limited fertility studies. The secretion of hCG starts in the preimplantation period as indicated by recent report on in vitro fertilized egg. hCG secreted by the embryo at 216 hours after fertilization was 3.8 mIU/ml requiring 0.4 ng/ml hCG binding capacity of antibodies, if the interception was to take place at the preimplantation stage. At the early post-implantation stage, hCG determined by specific βhCG radioimmunoassay at 4–4.5 weeks after LMP is reported to be 353±89 mIU/ml demanding 35 to 60 ng/ml of anti-hCG antibodies. Monkeys immunized with (αoLH.βhCG)-TT and having high antibody titers kept on ovulating with fertility setting in at 30–140 ng/ml of anti-hCG antibodies. Due note has to be taken of the low cross-reaction of hCG antibodies with primate CG.

The use of mixed carriers is beneficial to evoke good response in those subjects who are poor responders to a given carrier. CHB is a good supplement to TT. Other carriers such as hepatitis B and sporozoite coat protein of *P. falciparum* are also believed to be beneficial. The use of carriers with immunoprophylactic potential is in consonance with the original concept in design of the βhCG-TT vaccine, where attempt was made to align the response to a reproductive hormone with antibodies of immunoprophylactic benefit.

Immunization against fertility can also be effected by a polyvalent vaccine which includes a sperm antigen (such as LDH-C₄) used either as a carrier linked for example to βhCG as shown in Table 6, or used together with a carrier such as tetanus toxoid. Table 6 shows the reduced fertility in female mice when immunized with a vaccine of LDH-C₄ linked to βhCG.

TABLE 1

Cumulative antibody response above 60 ng hCG binding capacity per ml serum and its duration in monkeys immunized with βoLH-TT and βoLH-TT-hCG.

| Monkey No. | Immunogen (No. of Injections) | Area under the Curve >60 ng/ml | Duration (weeks) |
|---|---|---|---|
| 104 | βoLH-TT | 1575 | 35 |
| 105 | (3) | 900 | 11 |
| 106 |  | 550 | 20 |
| Mean + SEM |  | 1008 + 300 | 22 + 7 |
| 88 | βoLH-TT-hCG | 5470 | 28 |
| 92 | (3) | 16310 | 48 |
| 94 |  | 19580 | 58 |
| Mean + SEM |  | 13786 + 4269 | 43 + 7 |

TABLE 1a

Cumulative Antibody response above 60 ng hCG binding capacity per ml and its duration in monkeys immunized with (αoLH.βhCG)-TT and βhCG-TT

| Monkey No. | Immunogen | Number of injections | Area under the curve >60 ng/ml | Duration (weeks) |
|---|---|---|---|---|
| 82 | βhCG-TT | 4 | 2900 | 29 |
| 84 |  | 4 | 3850 | 30 |
| 87 |  | 4 | 4020 | 26 |

TABLE 1a-continued

Cumulative Antibody response above 60 ng hCG binding capacity per ml and its duration in monkeys immunized with (αoLH.βhCG)-TT and βhCG-TT

| Monkey No. | Immunogen | Number of injections | Area under the curve >60 ng/ml | Duration (weeks) |
|---|---|---|---|---|
| Mean + SEM |  |  | 3590 + 285 | 27 + 1 |
| 96 | (αoLH.βhCG)-TT | 3 | 41610 | 52 |
| 100 |  | 3 | 18820 | 52 |
| 101 |  | 3 | 19825 | 35 |
| Mean + SEM |  |  | 26752 + 6078 | 46 + 5 |

TABLE 2

Association constant (Ka) of anti-gonadotropin antibodies produced by βoLH-TT and βoLH-TT-βhCG

| Monkey No. | Immunogen | Ka $M^{-1} \times 10^{-9}$ |
|---|---|---|
| 88 | βoLH-TT-βhCG | 7.0 |
| 89 |  | 5.0 |
| 92 |  | 26.9 |
| 94 |  | 63.0 |
| 104 | βoLH-TT | 31.0 |
| 105 |  | 22.8 |
| 106 |  | 9.0 |
| 107 |  | 6.3 |
| 108 |  | 10.6 |

Serum analysed on day 182 or 200 after the start of immunization.

TABLE 2a

Association contact (Ka) of anti-hCG antibodies produced by vaccine (αoLH.βhCG)-TT

| Monkey Number | Association constant (Ka, $M^{-1} \times 10^{-9}$) |
|---|---|
| 96 | 2.0 |
| 99 | 1.1 |
| 100 | 12.8 |
| 101 | 20.8 |
| 102 | 7.7 |

Serum analysed on day 200 after the start of immunization

TABLE 3a

Cross reactivity of anti-hCG sera generated by αoLH. βhCG—TT with human LH, FSH and TSH

| Antiserum | % specific binding with iodinaed tracer | | | |
|---|---|---|---|---|
|  | hCG | hLH | hFSH | hTSH |
| Control (specific) | 70 | 67 | 33 | 26 |
| Monkey |  |  |  |  |
| 96 | 54 | 42 | 0 | 0 |
| 99 | 21 | 14 | 0 | 0 |
| 100 | 57 | 25 | 0 | 0 |
| 101 | 34 | 19 | 0 | 0 |
| 102 | 15 | 12 | 0 | 0 |
| Mean + SEM | 36 + 7 | 22 + 5 | 0 | 0 |

The bleeds tested were of day 67 after primary immunization. Direct binding with radioiodinated hormones was determined with serum samples at 1:200 final dilution.

% specific binding = $\frac{\text{(Bound counts − Nonspecific counts)}}{\text{Total counts}} \times 100$

TABLE 4

Anti-hCG Titers Preventing Pregnancy

| Monkey | Formulation | Cycles Mated | Anti-hCG titers ng/ml |
|---|---|---|---|
| 92 | βhCG-TT-βoLH | 6 | 80–600 |
| 94 | βhCG-TT-βoLH | 3 | 110–800 |
| 96 | (αoLH.βhCG)-TT | 6 | 400–2600 |
| 101 | (αoLH.βhCG)-TT | 3 | 650–900 |
| 109 | βhCG-TT + βoLH-TT | 1 | 400 |

TABLE 5

Anti-hCG Titers Not Preventing Pregnancy

| Monkey | Formulation | Anti-hCG Titers ng/ml |
|---|---|---|
| 88 | βhCG-TT-βoLH | 35 |

TABLE 3

Reactivity of antigonadotropin sera with hLH, FSH and hTSH

| Antiserum | Immunogen | % Specific binding with iodinated tracer | | | |
|---|---|---|---|---|---|
|  |  | hCG | hLH | hFSH | hTSH |
| Control with sera specific to various hormones |  | 70 | 67 | 33 | 26 |
| Monkey |  |  |  |  |  |
| 88 | βoLH—TT—βhCG | 37 | 26 | 0 | 0 |
| 89 |  | 22 | 15 | 0 | 0 |
| 92 |  | 51 | 33 | 0 | 0 |
| 93 |  | 18 | 15 | 0 | 0 |
| 94 |  | 47 | 35 | 0 | 0 |
| Mean + SEM |  | 35 + 6.5 | 25 + 4 | 0 | 0 |
| 104 |  | 12 | 12 | 0 | 0 |
| 105 |  | 19 | 13 | 0 | 0 |
| 106 | βoLH—TT | 20 | 13 | 0 | 0 |
| 107 |  | 11 | 11 | 0 | 0 |
| 108 |  | 13 | 11 | 0 | 0 |
| Mean + SEM |  | 15 + 2 | 12 + 0.5 | 0 | 0 |

The bleeds tested were of day 67 after primary immunization. Direct binding with radioiodinated hormones was determined with the serum samples at 1:200 final dilution.

% specific binding = $\frac{\text{(Bound Counts − Non-specific counts)}}{\text{Total Counts}} \times 100$ TABLE 5-continued

| Anti-hCG Titers Not Preventing Pregnancy | | |
|---|---|---|
| Monkey | Formulation | Anti-hCG Titers ng/ml |
| 89 | βhCG-TT-βoLH | 5 |
| 99 | (αoLH.βhCG)-TT | 30 |
| 100 | (αoLH.βhCG)-TT | 140 |
| 110 | βhCG-TT + βoLH-TT | 45 |
| 111 | βhCG-TT + βoLH-TT | 110 |
| 113 | βhCG-TT + βoLH-TT | 5 |

TABLE 6

Effect of Active Immunization of LDH-$C_4$ on the Fertility of BALB/c Mouse

| Sex | Number of Animals | Antigen Adjuvant | Dose Route | Number of Immunization | First* Delivery | Second* Delivery |
|---|---|---|---|---|---|---|
| MALE | 8 | LDH-$C_4$ | 10 ug | 2 | 7/8 | 8/8 |
| | | CFA, IFA | SC | | | (Vaginal plug positive) |
| FEMALE | 9 | LDH-$C_4$ | 10 ug | 2 | 0/9 | 2/8 |
| | | CFA, IFA | SC | | | (Vaginal plug positive) |

*Mating with non-immunized partners of proven fertility.

What I claim as my invention is:

1. A process for the preparation of a polyvalent vaccine which comprises the steps of:
   (a) obtaining at least two seprate antigens of the rerproductive system, a first being a preparation of βsubunit of hCG and a second being a preparation of a sperm antigen or a heterospecies α or β subunit of LH,
   (b) obtaining an immunologically pure preparation of at least one subject-compatible carrier,
   (c) conjugating at least two antigens of step (a) with at least one carrier of step (b) by carrying out at least one step selected from the group consisting of
      (i) forming a composite conjugate of at least two separate antigens linked to the same carrier moiety,
      (ii) forming a physical mixture of conjugates of at least two separate antigens each separately linked to at least one carrier,
      (iii) associating at least two separate antigens which are βsubunit of hCG and a heterospecies αsubunit to form an annealed composite and subsequently conjugating the annealed composite with a carrier, and,
      (iv) forming a polyvalent conjugate of at least one antigen linked both to at least one sperm antigen and to at least one carrier, and,
      (v) where more than one carrier is present, forming a conjugate of one of said antigens linked to a said carrier.

2. A process according to claim 1 wherein, in steps (i), (ii) and (v), said βhCG is present as an annealed composite with a heterospecies αsubunit.

3. A process according to claim 1, wherein one of said antigens is a sperm antigen.

4. A process according to claim 1, wherein more than one subject-compatible carrier is used.

5. A process according to claim 1, wherein said at least two separate antigens are hormonal subunits, or fragments thereof.

6. A process according to claim 1, wherein said at least two separate antigens are βoLH and βhCG.

7. A process according to claim 1, wherein two subject-compatible carriers are present.

8. A process according to claim 1, wherein said subject-compatible carrier is one or more members selected from the group consisting of tetanus toxoid, cholera toxin B-chain, hepatitis B surface protein, a malaria protein, diphtheria toxoid and sporozoite coat protein of *P. falciparum*.

9. A process according to claim 1, wherein tetanus toxoid and cholera toxin B-chain are present as carriers.

10. A process according to claim 1, wherein said polyvalent vaccine is mixed with an adjuvant selected from the group consisting of alum, detoxified sodium phthalyl derivative of salmonella lipopolysaccharide (SPLPS) and 6-o-dipalmitoyl-glyceryl-succinyl (MDP).

11. A process for the preparation of a polyvalent vaccine for a mammalian subject having a low antibody response to a single conjugate vaccine which comprises the steps of
   (a) obtaining at least two separate antigens of the reproductive system, a first being a preparation of βsubunit hCG and a second being a preparation of a sperm antigen or heterospecies α or βsubunit of LH,
   (b) obtaining an immunologically pure preparation of at least two subject-compatible carriers,
   (c) conjugating at least two antigens of step (a) with at least one carrier of step (b) by carrying out at least one step selected from the group consisting of
      (i) forming a composite conjugate of at least two separate antigens linked to the same carrier moiety,
      (ii) forming a physical mixture of conjugates of at least two separate antigens separately linked to at least one of said carriers,
      (iii) associating at least two separate antigens which are βsubunit of hCG and a said heterospecies αsubunit to form an annealed composite and subsequently conjugating the annealed conjugate with at least one of said carriers,
      (iv) forming a polyvalent conjugate of at least one antigen linked both to at least one sperm antigen and to at least one carrier, and,
      (v) forming a conjugate of one of said antigens linked to a carrier, and
   (d) combining two or more conjugate products from steps (i) to (v) above.

12. A polyvalent birth control vaccine which comprises an effective amount of at least two antigens of the reproductive system with the proviso that in the case of homospecies antigens the antigens are specific to the reproductive system and at least one subject-compatible carrier said polyvalent vaccine being selected from the group consisting of:
   (i) a composite conjugate of at least two separate antigens linked to the same carrier moiety (ii) a mixture of conjugates of at least two separate antigens each separately linked to at least one carrier (iii) an annealed composite of at least two separate antigens which are βsubunit of hCG and a heterospecies αsubunit; conjugated to a carrier, (iv) a polyvalent conjugate of at least one antigen linked to sperm antigen and to at least one carrier, and, (v) a mixture of at least two of (i) to (iv).

13. A polyvalent birth control vaccine which comprises an effective amount of at least two antigens of the reproductive system, a first being from a preparation of βsubunit of hCG and a second being a preparation of a sperm antigen or a heterospecies α or βsubunit of LH, and at least one subject-compatible carrier, said polyvalent vaccine being selected from the group consisting of:

(i) a composite conjugate of at least two separate antigens linked to the same carrier moiety (ii) a mixture of conjugates of at least two separate antigens each separately linked to at least one carrier (iii) an annealed composite of at least two separate antigens which are βsubunit of hCG and a heterospecies αsubunit; conjugated to a carrier, (iv) a polyvalent conjugate of at least one antigen linked to sperm antigen and to at least one carrier, and, (v) a mixture of at least two of (i) to (iv).

14. The polyvalent vaccine of claim 13 wherein in (i), (ii) and (v), said βhCG is present as an annealed composite with a heterospecies αsubunit.

15. The polyvalent vaccine of claim 13 wherein one of said antigens is a sperm antigen.

16. The polyvalent vaccine of claim 13 containing more than one subject-compatible carrier.

17. The polyvalent vaccine of claim 13 wherein at least two separate antigens are hormonal subunits, or fragments thereof.

18. The polyvalent vaccine of claim 13 wherein at least two separate antigens are βoLH and βhCG.

19. The polyvalent vaccine of claim 13 wherein two subject-compatible carriers are present.

20. The polyvalent vaccine of claim 13 wherein said subject compatible carrier is one or more members selected from the group consisting of tetanus toxoid, cholera toxin B-chain, hepatitis B surface protein, a malaria protein, diphtheria toxoid and sporozoite coat protein of *P. falciparum*.

21. The polyvalent vaccine of claim 13 wherein tetanus toxoid and cholera toxin B-chain are employed as carriers.

22. The polyvalent vaccine of claim 13 mixed with an adjuvant selected from the group consisting of alum, detoxified sodium phthalyl derivative of salmonella lipopolysaccharide (SPLPS) and 6-o-dipalmitoyl-glyceryl-succinyl (MDP).

23. The polyvalent vaccine of claim 13 comprising a mixture of at least one of αoLH.βhCG-TT and αoLH.βhCG-CHB with at least one of sperm antigen-CHB and sperm antigen-TT.

24. A method of birth control employing the polyvalent vaccine of claim 12 which comprises administering said vaccine to a female mammal at a dose and frequency sufficient to prevent pregnancy to term.

25. A method of birth control employing the polyvalent vaccine of claim 12 which comprises administering said vaccine to a female mammal at a dose and frequency sufficient to maintain an antibody titer to said vaccine of at least 60 ng/ml.

* * * * *